United States Patent [19]
Cascieri et al.

[11] Patent Number: 6,001,970
[45] Date of Patent: Dec. 14, 1999

[54] MODIFIED HUMAN NEUROPEPTIDE Y1 RECEPTORS

[75] Inventors: Margaret A. Cascieri, East Windsor; Douglas John MacNeil, Westfield; Catherine D. Strader, Verona, all of N.J.

[73] Assignee: Merck & Co., Inc, Rayway, N.J.

[21] Appl. No.: 08/817,869

[22] PCT Filed: Nov. 6, 1995

[86] PCT No.: PCT/US95/14377

§ 371 Date: May 6, 1997

§ 102(e) Date: May 6, 1997

[87] PCT Pub. No.: WO96/14331

PCT Pub. Date: May 17, 1996

Related U.S. Application Data

[63] Continuation-in-part of application No. 08/335,017, Nov. 7, 1994, abandoned.

[51] Int. Cl.[6] .................. C07K 14/705; C07H 21/04; C12P 15/11
[52] U.S. Cl. ........................................ 530/350; 536/23.5
[58] Field of Search ................ 435/7.1, 7.2, 320.1, 435/325, 69.1; 530/350; 536/23.5

[56] References Cited

U.S. PATENT DOCUMENTS

| | | |
|---|---|---|
| 5,264,565 | 11/1993 | England et al. |
| 5,288,607 | 2/1994 | Emorine et al. |
| 5,516,653 | 5/1996 | Bard et al. |
| 5,545,549 | 8/1996 | Gerald et al. |
| 5,571,695 | 11/1996 | Selbie et al. |
| 5,589,568 | 12/1996 | Higashijima et al. |
| 5,621,079 | 4/1997 | Cascieri et al. |

FOREIGN PATENT DOCUMENTS

WO 93/09227   5/1993   WIPO.

OTHER PUBLICATIONS

Colmers, *TINS*, vol. 21, p. 89, 1998.
Rudinger, In. *Peptide Hormones*, ed. Parsons, University Park Press, Baltimore, pp. 1–7, 1976.
Dohlman et al., *Annu. Rev. Biochem.*, vol. 60, pp. 653–688, 1991.
Cheung et al., *Febs Lett.*, vol. 279, pp. 277–280, 1991.
Allen, L.F. et al, "G–protein coupled recept or genes as protoocogenes: Coonsistively among mutation of the abha 18 adrenergic receptor enhances mircogenes and sumogenicity ", Proc. Natl. Acad. Sci. vol. 88, pp. 11354–11358, Dec. 1991.
Baldwin, J.M. "The probable arrangement of the helices in G protein–coupled receptors", The EMBO Journal, vol. 12, No. 4, pp. 1693–1703.
Cheung, A.H. et al. "Separation of the Structural Requirements for Agonist–Promoted Activation and Sequestration of the beta–adrenergic receptor,", Molecular Pharm. vol. 37, pp. 775–779.

Cotecchia S., et al. "Discrete Amino Acid Sequences of the alpha 1–adrenergic receptor determine the Selectivity of Coupling to Phosphoinositide Hydrolysis", The Journal of Biological Chemistry, vol. 267, No.3 pp.1633–1639.
Dixon, R. et al., "Ligand binding to the beta–adrenergic receptor involves it rhodopsin–like core", Nature, vol. 326, Mar. 5, 1987, pp. 73–77.
England, B.P., "A chimeric D2 dopamine/ml muscarinic receptor with D2 binding specificity mobilizes intracellular calcium in response to dopamine", FEBS 09352, Feb. 1991, vol. 279, No. 1, pp. 87–90.
Hausdorff, W.P. et al. "A Mutation of the Beta2–Adrenergic Receptor Impairs Agonist Activation of Adenylyl Cyclase without Affecting High Affinity Agonist Binding", vol. 265, pp. 1388–1393 1990.
Kjelsberg, M.A. et al. "Constitutive Activation of the alpha 1B–Adrenergic receptor by all Amino acid sustitutions at a single site", The Journal of Biological Chemistry, vol. 267, No. 3, pp. 1430–1433, 1992.
Kosugi, S. et al. "Mutation of Alanine 623 in the Third Cytoplasmic Loop of the Rat Tyrotropin (TSH) Receptor Results in a Loss in the Phosphoinositide but not cAMP signal induced by TSH and receptor Autoantibodies", The Journal of Biological Chemistry, vol. 267, pp. 24153–24156, 1992.
Liggett, S.B. et al. "Coupling of a Mutated Form of the Human Beta 2–Adrenergic Receptor to Gi and Gs", The Journal of Biological Chemistry, vol. 266. No. 8. pp. 4816–4821, 1991.
O'Dowd B.F. et al. "Site–directed Mutagenesis of the Cytoplasmic Domains of the Human beta 2–Adrenergic Receptor", The Journal of Biological Chemistry, vol. 263, No. 31, pp. 15985–15992. 1988.
Ohyama K. et al. "Domains for G–Protein Coupling in Angiotensin II Receptor type I: Studies by Site–Directed Mutagenesis", vol. 189, No. 2 1992, pp. 677–683.
Samama, P. et al. "A Mutation–induced Activated State of the Beta 2–Adrenergic Receptor", The Journal of Biological Chemistry, No. 7, Issue of Mar. 5. pp. 4625–4636, 1993.

(List continued on next page.)

*Primary Examiner*—Anthony C. Caputa
*Assistant Examiner*—Stephen Gucker
*Attorney, Agent, or Firm*—Melvin Winokur; Kenneth R. Walton

[57] ABSTRACT

Modified neuropeptide Y receptors having deletions, replacements or additions in the third intracellular domain are identified and methods of making the modified receptors are provided. The invention includes the modified receptors, assays employing the modified receptors, cells expressing the modified receptors, compounds identified through the use of the modified receptors, including modulators of the receptors, and the use of the compounds to treat conditions, including obesity, diabetes, anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases.

2 Claims, 4 Drawing Sheets

OTHER PUBLICATIONS

Strader, C.D. et al. "Mutations that Uncouple the Beta–Adrenergic Receptor from Gs and Increase Agonist Affinity", The Journal of Biological Chemistry, vol. 262, No. 4, pp. 16439–16443, 1987.

Weiss, J. et al. "Delineation of Muscarinic Receptor Domains Conferring Selectivity of Coupling to Guanine Nucleotide–Binding Proteins and Second Messengers", Molecular Pharmacology, vol. 38, pp. 517–523.

Wong, S. et al. "Chimeric Muscarinic Cholinergic: Beta–Adrenergic Receptors that Activate Gs in Response to Muscarinic Agonists", Jour. of Biol. Chem. vol. 265, No. 11, pp. 6219–6224, 1990.

Grundemar, L., et al., Characterization of vascular neuropeptide Y receptors Br. J. Pharmacol. 1992.105 (1):pp. 45–50.

Wahlestedt, C., et al., Evidence for different pre– and post–junctional receptors for neuropeptide Y and related peptides, Regul. Pept. 1986.13 (3–4):pp. 307–318.

Jorgensen et al., Structure–function studies on neuropeptide Y and pancreatic polypeptide—evidence for two PP–fold receptors in vas deferens, Eur. J. Pharmacol. 1990. 186 (1): pp. 105–114.

Cox, H.M., et al., The Effects of Selective Amino Acid Substitution Upon Neuropeptide Y Antisecretory Potency in Rat Jejunum Mucosa. Peptides, 1991. 12(2):pp. 323–327.

Wahlestedt, C., et al., Identification of Cultured Cells Selectively Expressing Y1–, Y2–, or Y3–Type Receptors for Neuropeptide Y/Peptide YY. Life Sciences, 1992.50:pp. PL7–PL12.

Balasubrananian, A., et al., Characterization of Neuropeptide Y Binding Sites in Rat Cardiac Ventricular Membranes 1, Peptides 1990. 11(3):pp. 545–550.

Li, X.J., et. al., Cloning, Functional Expression, and Developmental Regulation of a Neuropeptide Y Receptor from Drosophila melangaster, J. Biol. Chem., 1992. 267(1):pp. 9–12.

Jolicoeur, F.B., In Vivo Structure Activity Study Supports the Existence of Heterogeneous Neuropeptide Y Receptors, Brain Res. Bull., 1991. 26(2):pp. 309–311.

Liebowitz & Alexander, Analysis of Neuropeptide Y–Induced Feeding: Dissociation of Y1 and Y2 Receptor Effects on Natural Meal Patterns, Peptides, 1991. 12(6):pp. 1251–1260.

Herzog, H., et al., Cloned human neuropeptide Y receptor couples to two different second messenger systems, Proc. Natl. Acad. Sci., USA, 1992, vol. 89, pp. 5794–5798.

Larhammar, D., et al., Cloning and Functional Expression of a Human Neuropeptide Y/Peptide YY Receptor of the Y1 Type, J. of Biol. Chem., 1992. vol. 267, No. 16:pp. 10935–10938.

Eva, C., et al.. Molecular cloning of a novel G protein–coupled receptor that may belong to the neuropeptide receptor family, FEBS, 1990. vol. 271, No. 1,2: pp. 81–84.

Wahlestedt, C., et al., Neuropeptide Y–related peptides and their receptors—are the receptors potential therapeutic drug targets?, Ann. Rev. Pharmacol. Toxicol., 1993. 32:pp. 309–352.

Ren et al., Constitutively Active Mutants of the Alpha 2–Adrenergic Receptor, J. Biol. Chem., 268 (22): 16483–16487 (1993).

Prossnitz et al., The Role of the Third Intracellular Loop of the Neutrophil N–Formyl Peptide Receptor in G Protein Coupling, Biochem. J., 294:581–587 (1993).

```
  1  .....MGPPGNDSDFLLTTNGSHVPDHDVTEERDE.....AWVVGMAILM   40
          :...:|.|   :.||.  .: :.|.|:      |:..:|:
  1  MNSTLFSQVENHS...VHSNFSEKNAQLLAFENDDCHLPLAMIFTLALAY   47

41  SVIVLAIVFGNVLVITAIAKFERLQTVTNYFITSLACADLVMGLAVVPFG   90
     :..::: | ||: :|. | | .:..|||.:|..|. .||::::  ..:|:.
 48  GAVIILGVSGNLALIIIILKQKEMRNVTNILIVNLSFSDLLVAIMCLPLT   97

91  ASHILMKMWNFGNFWCEFWTSIDVLCVTASIETLCVIAVDRYIAITSPFK  140
     ..||. | ||:  |.:. ::.::::|.||  .|.:|·|:|.  |..|
 98  FVYTLMDHWVFGEAMCKLNPFVQCVSITVSIFSLVLIAVERHQLIINPRG  147

141  YQSLLTKNKARMVILMVWIVSGLTSFLPIQMHWYRATHQKAIDCY HKET  189
     :..      ..  :...:  |: |.: .||  .|:    : :.  ..:|.| .| .
148  WRPNNRHAYVGIAVIWVLAVASSLPFLIYQVMTDEPFQNVTLDAYKDKYV  197

190  CCDFFTNQ....AYAIASSIVSFYVPLVVMVFVYSRVFQVAKRQLQKIDK  235
     | | |..:    .|..    :: ::.||......| :::    ||. ...:||
198  CFDQFPSDSHRLSYTTLLLVLQYFGPLCFIFICYFKIYIRLKRRNNMMDK  247

236  SEGRFHSPNLGQVEQDGRSGHGLRRSSKFCLKEHKALKTLGI.IMGTFTL  284
                                   .|..|:  .| |  :...: : |:..|.:
248  ..........................MRDNKYRSSETKRINIMLLSIVVAFAV  274

285  CWLPFFIVNIVHVIQDNLIP....KEVYILLNWLGYVNSAFNPLIYC.RS  329
     ||||: |.|.|   ...:|:     .:::|  ::   : :.....||::|.
275  CWLPLTIFNTVFDWNHQIIATCNHNLLFLLCHLTAMISTCVNPIFYGFLN  324

330  PDFRIAFQELLCLRRSSSKAYGNGYSSNSNGKTDY....MGEASGCQL..  373
     ..|. ..:|  ::: :    .|::  :    | .||    : :||...:
325  KNFQRDLQFFFNFCDFRSRDDDYETIAMSTMHTDVSKTSLKQASPVAFKK  374

374  ·GQEKESERLCEDPPGTESFVNCQGTVPSLSLDSQGRNCSTNDSPLX    419
          ......|::
375  INNNDDNEKIX..........................             385
```

FIG. 3

```
                            SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ile Tyr Ile Arg Leu Lys Arg Arg Asn Asn Met Met
1               5                   10

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Lys Met Arg Asp Asn Lys Tyr Arg Ser Ser Glu Thr Lys
1               5                   10

(2) INFORMATION FOR SEQ ID NO:3:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Asn Ser Thr Leu Phe Ser Gln Val Glu Asn His Ser Asp Phe Leu
1               5                   10                  15

Val His Ser Asn Phe Ser Glu Lys Asn Ala Gln Leu Leu Ala Phe Glu
                20                  25                  30

Asn Asp Asp Cys His Leu Pro Leu Ala Met Ile Phe Thr Leu Ala Leu
            35                  40                  45

Ala Tyr Gly Ala Val Ile Ile Leu Gly Val Ser Gly Asn Leu Ala Leu
        50                  55                  60

Ile Ile Ile Ile Leu Lys Gln Lys Glu Met Arg Asn Val Thr Asn Ile
```

```
              65                  70                  75                  80
Leu Ile Val Asn Leu Ser Phe Ser Asp Leu Val Ala Ile Met Cys
                    85                  90                  95

Leu Pro Leu Thr Phe Val Tyr Thr Leu Met Asp His Trp Val Phe Gly
                   100                 105                 110

Glu Ala Met Cys Lys Leu Asn Pro Phe Val Gln Cys Val Ser Ile Thr
                115                 120                 125

Val Ser Ile Phe Ser Leu Val Leu Ile Ala Val Glu Arg His Gln Leu
            130                 135                 140

Ile Ile Asn Pro Arg Gly Trp Arg Pro Asn Asn Arg His Ala Tyr Val
145                 150                 155                 160

Gly Ile Ala Val Ile Trp Val Leu Ala Val Ala Ser Ser Leu Pro Phe
                165                 170                 175

Leu Ile Tyr Gln Val Met Thr Asp Glu Pro Phe Gln Asn Val Thr Leu
                180                 185                 190

Asp Ala Tyr Lys Asp Lys Tyr Val Cys Phe Asp Gln Phe Pro Ser Asp
                195                 200                 205

Ser His Arg Leu Ser Tyr Thr Thr Leu Leu Leu Val Leu Gln Tyr Phe
            210                 215                 220

Gly Pro Leu Cys Phe Ile Phe Ile Cys Tyr Phe Lys Ile Tyr Ile Arg
225                 230                 235                 240

Leu Lys Arg Arg Asn Asn Met Met Asp Lys Ser Glu Gly Arg Phe His
                245                 250                 255

Ser Pro Asn Leu Gly Gln Val Glu Gln Asp Gly Arg Ser Gly His Gly
                260                 265                 270

Leu Met Arg Asp Asn Lys Tyr Arg Ser Ser Glu Thr Lys Arg Ile Asn
            275                 280                 285

Ile Met Leu Leu Ser Ile Val Val Ala Phe Ala Val Cys Trp Leu Pro
            290                 295                 300

Leu Thr Ile Phe Asn Thr Val Phe Asp Trp Asn His Gln Ile Ile Ala
305                 310                 315                 320

Thr Cys Asn His Asn Leu Leu Phe Leu Leu Cys His Leu Thr Ala Met
                325                 330                 335

Ile Ser Thr Cys Val Asn Pro Ile Phe Tyr Gly Phe Leu Asn Lys Asn
                340                 345                 350

Phe Gln Arg Asp Leu Gln Phe Phe Phe Asn Phe Cys Asp Phe Arg Ser
                355                 360                 365

Arg Asp Asp Asp Tyr Glu Thr Ile Ala Met Ser Thr Met His Thr Asp
            370                 375                 380

Val Ser Lys Thr Ser Leu Lys Gln Ala Ser Pro Val Ala Phe Lys Lys
385                 390                 395                 400

Ile Asn Asn Asn Asp Asp Asn Glu Lys Ile Xaa
                405                 410
```

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Lys Ile Arg Asp Ser Lys Tyr Arg Ser Ser Glu Thr Lys
1               5                  10
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ile Trp Ser Lys Leu Lys Asn His Val Ser Pro Gly
1               5                   10
```

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ala Asn Asp His Tyr His Gln Arg Arg Gln Lys Thr Thr
1               5                   10
```

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala Ala Ser Asp His Tyr His Gln Arg Arg His Lys Thr Thr
1               5                   10
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ile Tyr Arg Arg Leu Gln Arg Gln Gly Arg Val Phe
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ile Tyr Gln Arg Leu Gln Arg Gln Arg Arg Ala Phe
1               5                   10
```

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
His Lys Gly Thr Tyr Ser Leu Arg Ala Gly His Met Lys
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
His Thr His Thr Cys Ser Ser Arg Val Gly Gln Met Lys
1               5                   10
```

(2) INFORMATION FOR SEQ ID NO:12:

(i) SEQUENCE CHARACTERISTICS:
        (A) LENGTH: 418 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Met Gly Pro Pro Gly Asn Asp Ser Asp Phe Leu Leu Thr Thr Asn Gly
1               5                   10                  15

Ser His Val Pro Asp His Asp Val Thr Glu Glu Arg Asp Glu Ala Trp
                20                  25                  30

Val Val Gly Met Ala Ile Leu Met Ser Val Ile Val Leu Ala Ile Val
            35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ser His Ile Leu Met
                85                  90                  95

Lys Met Trp Asn Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
            115                 120                 125

Val Asp Arg Tyr Ile Ala Ile Thr Ser Pro Phe Lys Tyr Gln Ser Leu
    130                 135                 140

Leu Thr Lys Asn Lys Ala Arg Met Val Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Lys Ala Ile Asp Cys Tyr His Lys Glu Thr Cys Cys Asp
```

```
                        180                 185                 190
Phe Phe Thr Asn Gln Ala Tyr Ala Ile Ala Ser Ser Ile Val Ser Phe
            195                 200                 205

Tyr Val Pro Leu Val Val Met Val Phe Val Tyr Ser Arg Val Phe Gln
    210                 215                 220

Val Ala Lys Arg Gln Leu Gln Lys Ile Asp Lys Ser Glu Gly Arg Phe
225                 230                 235                 240

His Ser Pro Asn Leu Gly Gln Val Glu Gln Asp Gly Arg Ser Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Pro
        290                 295                 300

Lys Glu Val Tyr Ile Leu Leu Asn Trp Leu Gly Tyr Val Asn Ser Ala
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Ser Lys Ala Tyr Gly Asn
            340                 345                 350

Gly Tyr Ser Ser Asn Ser Asn Gly Lys Thr Asp Tyr Met Gly Glu Ala
        355                 360                 365

Ser Gly Cys Gln Leu Gly Gln Glu Lys Glu Ser Glu Arg Leu Cys Glu
        370                 375                 380

Asp Pro Pro Gly Thr Glu Ser Phe Val Asn Cys Gln Gly Thr Val Pro
385                 390                 395                 400

Ser Leu Ser Leu Asp Ser Gln Gly Arg Asn Cys Ser Thr Asn Asp Ser
                405                 410                 415

Pro Leu
```

MODIFIED HUMAN NEUROPEPTIDE Y1 RECEPTORS

This application is a 371 application of PCT/US95/14377, filed Nov. 6, 1995 and is a continuation-in-part of U.S. Ser. No. 08/335,017, filed Nov. 7, 1994, now abandoned, the contents of which are hereby incorporated by reference.

BACKGROUND OF THE INVENTION

Neuropeptide Y (NPY) is a 36 residue, amidated peptide. It is anatomically co-distributed and co-released with norepinephrine in and from sympathetic postganglionic neurons ([1], [2], [3], [4], [5], [6]). Stimulation of the sympathetic nervous system under physiological circumstances such as exercise ([7], [8]) or exposure to the cold ([9], [10]) promotes an elevation of both norepinephrine and NPY.

NPY is believed to act in the regulation of appetite control ([11], [12]) and vascular smooth muscle tone ([13], [14]) as well as regulation of blood pressure ([6], [15], [16], [17]). NPY also decreases cardiac contractility ([18], [19], [20], [21], [22]). Congestive heart failure and cardiogenic shock are associated with probable releases of NPY into the blood ([23], [24], [25]). Regulation of NPY levels may be beneficial to these disease states [26].

At the cellular level, neuropeptide Y binds to a G-protein coupled receptor ([27], [28], [29], [30]). Neuropeptide Y is involved in regulating eating behavior and is an extremely potent orixigenic agent ([11], [12], [31]). When administered intracerebroventricularly or injected into the hypothalamic paraventricular nucleus (PVN) it elicits eating in satiated rats ([32], [33], [34]) and intraventricular injection of antisera to NPY decreases eating ([11], [31]). It has been shown to stimulate appetite in a variety of species and at different stages of development ([12]). Other effects on energy metabolism include decreased thermogenesis, body temperature and uncoupling protein, and increased white fat storage and lipoprotein lipase activity ([9], [35], [36], [37], [38], [39]). NPY levels in the PVN increase upon fasting ([40], [41], [42], [43], [44]), before a scheduled meal ([31], [36], [40]), and in both streptozotocin-induced and spontaneous diabetes ([36], [45], [46], [47], [48], [49]). Also, NPY levels are increased in genetically obese and hyperphagic Zucker rats ([36], [50], [51]). Thus, a specific centrally acting antagonist for the appropriate NPY receptor subtype may be therapeutically useful for treating obesity and diabetes. Other disorders which might be targeted therapeutically include anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases ([26], [52]).

At least four receptor subtypes of the NPY family have been proposed based on pharmacological and physiological properties. The Y1 receptor is stimulated by NPY or PYY (peptide YY) and appears to be the major vascular receptor ([16], [53], [54], [55]). The Y2 receptor is stimulated by C-terminal fragments of NPY or PYY and is abundantly expressed both centrally and peripherally ([55], [56], [57], [58]). A third receptor (Y3) is exclusively responsive to NPY and is likely present in adrenal medulla, heart, and brain stem ([27], [59]). In addition, other subtypes of this receptor family are known to exist, based on pharmacological and physiological characterization ([60], [61], [62], [63]). The feeding behavior is stimulated potently by NPY, $NPY_{2-36}$ and the Y1 agonist [Leu31, Pro34]NPY, but is not stimulated by the Y2 agonist $NPY_{13-36}$ ([11], [64], [65], [66]). This pharmacology is not characteristic of the defined Y1, Y2 or Y3 receptors and can thus be attributed to a unique receptor, termed "atypical Y1" ([11], [65], [66]), that is responsible for evoking the feeding response. In addition, data indicate the existence of additional members of this receptor family including one subtype specific for peptide PP ([62], [63]), one with affinity for short C-terminal fragments of NPY which induce hypotension when administered systemically ([15], [17], [30], [67], [68]), and one associated with binding of NPY and PYY to brain sigma and phencyclidine binding sites ([61]).

The DNA encoding the Y 1 receptor has been cloned and shown to be a G protein coupled receptor ([53], [69], [70]). G-protein coupled receptors are well-known to share substantial sequence homology to each other (71). Recently, DNA encoding the Y4 receptor has been isolated using Y1 DNA probes [72]. In addition, DNA encoding the Y2 receptor has been isolated by expression cloning ([73], [74]). The cDNAs encoding these receptors are at least 45% identical at the DNA level and 30% at the protein level. Other NPY receptors have not been cloned.

REFERENCES

1. DeQuidt, M. E. and P. C. Emson, Distribution of neuropeptide Y-like immunoreactivity in the rat central nervous system-II. Immunohistochemical analysis. Neuroscience, 1986. 18(3): p. 545–618.
2. Lundberg, J. M., et al., Co-release of neuropeptide Y and catecholamines during physical exercise in man. Biochem Biophys Res Commun, 1985. 133(1): p. 30–6.
3. Morris, M. J., et al., Increases in plasma neuropeptide Y concentrations during sympathetic activation in man. J Auton Nerv Syst, 1986. 17(2): p. 143–9.
4. Pemow, J., Co-release and functional interactions of neuropeptide Y and noradrenaline in peripheral sympathetic vascular control. Acta Physiol Scand Suppl, 1988. 568(1): p. 1–56.
5. Sawchenko, P. E., et al., Colocalization of neuropeptide Y immunoreactivity in brainstem catecholaminergic neurons that project to the paraventricular nucleus of the hypothalamus. J Comp Neurol, 1985. 241(2): p. 138–53.
6. Wahlestedt, C., et al., Norepinephrine and neuropeptide Y: vasoconstrictor cooperation in vivo and in vitro. Am J Physiol, 1990. 258: p. R736–R742.
7. Kaijser, L., et al., Neuropeptide Y is released together with noradrenaline from the human heart during exercise and hypoxia. Clin Physiol, 1990. 10(2): p. 179–88.
8. Lewis, D. E., et al., Intense exercise and food restriction cause similar hypothalamic neuropeptide Y increases in rats. Am J Physiol, 1993. 264: p. E279–E284.
9. McCarthy, H. D., et al., Widespread increases in regional hypothalamic Neuropeptide- Y levels in acute Cold-Exposed rats. Neuroscience, 1993. 54(1): p. 127–132.
10. Zukowska, G. Z. and A. C. Vaz, Role of neuropeptide Y (NPY) in cardiovascular responses to stress. Synapse, 1988. 2(3): p. 293–8.
11. Stanley, B. G., et al., Evidence for neuropeptide Y mediation of eating produced by food deprivation and for a variant of the Y1 receptor mediating this peptide's effect. Peptides, 1992. 13: p. 581–587.
12. Stanley, B. G., Neuropeptide Y in multiple hypothalamic sites controls eating behavior, endocrine, and autonomic systems for body energy balance, in Neuropeptide Y, W. F. Colmers and C. Wahlestedt, Editor. 1993, Humana Press: Totowa, N.J. p. 457–509.
13. Abel, P. W. and C. Han, Effects of neuropeptide Y on contraction, relaxation, and membrane potential of rabbit cerebral arteries. J Cardiovasc Pharmacol, 1989. 13(1): p. 52–63.

14. Han, C. and P. W. Abel, Neuropeptide Y potentiates contraction and inhibits relaxation of rabbit coronary arteries. J Cardiovasc Pharmacol, 1987. 9(6): p. 675–81.

15. Grundemar, L., et al., Biphasic blood pressure response to neuropeptide Y in anesthetized rats. Eur J Phannacol, 1990. 179(1-2): p. 83–7.

16. Grundemar, L., et al., Characterization of vascular neuropeptide Y receptors. Br J Pharmacol, 1992. 105(1): p. 45–50.

17. Shen, S. H., et al., C-terminal neuropeptide Y fragments are mast cell-dependent vasodepressor agents. Eur. J. Phamacol., 1993. 204: p. 249–256.

18. Tseng, C. J., et al., Cardiovascular effects of neuropeptide Y in rat brainstem nuclei. Circ Res, 1989. 64(1): p. 55–61.

19. Carter, D. A., M. Vallejo, and S. L. Lightrnan, Cardiovascular effects of neuropeptide Y in the nucleus tractus solitarius of rats: relationship with noradrenaline and vasopressin. Peptides, 1985. 6(3): p. 421–5.

20. Grundemar, L., C. Wahlestedt, and D. J. Reis, Neuropeptide Y acts at an atypical receptor to evoke cardiovascular depression and to inhibit glutamate responsiveness in the brainstem. J Phannacol Exp Ther, 1991. 258(2): p. 633–8.

21. Grundemar, L., C. Wahlestedt, and D. J. Reis, Long-lasting inhibition of the cardiovascular responses to glutamate and the baroreceptor reflex elicited by neuropeptide Y injected into the nucleus tractus solitarius of the rat. Neurosci Lett, 1991. 122(1): p. 135–9.

22. Zukowska-Grojec, Z. and C. Wahlestedt, Origin and actions of neuropeptide Y in the cardiovascular system, in Neuropeptide Y, W. F. Colners and C. Wahlestedt, Editor. 1993, Humana Press: Totowa, N.J. p.315–388.

23. Edvinsson, L., et al., Congestive heart failure: involvement of perivascular peptides reflecting activity in sympathetic, parasympathetic and afferent fibres. Eur J Clin Invest, 1990. 20(1): p. 85–9.

24. Franco, C. A., et al., Release of neuropeptide Y and noradrenaline from the human heart after aortic occlusion during coronary artery surgery. Cardiovasc Res, 1990. 24(3): p. 242–6.

25. Maisel, A. S., et al., Elevation of plasma neuropeptide Y levels in congestive heart failure. Am J Med, 1989. 86(1): p. 43–8.

26. Wahlestedt, C. and D. J. Reis, Neuropeptide Y-relatedpeptides and their receptors—are the receptors potential therapeutic drug targets? Annu. Rev. Pharmacol. Toxicol., 1993. 32: p. 309–352.

27. Wahlestedt, C., S. Regunathan, and D. J. Reis, Identification of cultured cells selectively expressing Y1-, Y2-, or Y3-type receptors for neuropeptide Ylpeptide YY. Life Sciences, 1992. 50: p. PL7–PL12.

28. Feth, F., W. Rascher, and M. C. Michel, G-protein coupling and signalling of Y1-like neuropeptide Y receptors in SK-N-MC cells. Naunyn Schmiedebergs Arch Pharmacol, 1991. 344(1): p. 1–7.

29. Motulsky, H. J. and M. C. Michel, Neuropeptide Y mobilizes Ca2+ and inhibits adenylate cyclase in human erythroleukemia cells. Am J Physiol, 1988. 255: p. E880–E885.

30. Wahlestedt, C., et al., Neuropeptide Y receptor subtypes, Y1 and Y2. Ann N Y Acad Sci, 1990. 611(7): p. 7–26.

31. Sahu, A. and S. P. Kalra, Neuropeptidergic regulation of feeding-behavior—neuropeptide-Y. Trends In Endocrinology And Metabolism, 1993. 4(7): p. 217–224.

32. Clark, J. T., et al., Neuropeptide Y and human pancreatic polypeptide stimulate feeding behavior in rats. Endocrinology, 1984. 115(1): p. 427–429.

33. Stanley, B. G. and S. F. Leibowitz, Neuropeptide Y injected in the paraventricular hypothalamus: a powerful stimulant of feeding behavior. Proc. Natl. Acad. Sci. USA, 1985. 82: p. 3940–3943.

34. Stanley, B. G. and S. F. Leibowitz, Neuropeptide Y: stimulation of feeding and drinking by injection into the paraventricular nucleus. Life Sci, 1984. 35(26): p. 2635–42.

35. Zajevski, N., et al., Chronic intracerebroventricular neuropeptide-Y administration to normal rats mimics hormonal and metabolic changes of obesity. Endocrinology, 1993. 133(4): p. 1753–1758.

36. Billington, C. J. and A. S. Levine, Hypothalamic neuropeptide Y regulation of feeding and energy metabolism. Current Opinion in Neurobiology, 1992. 2: p. 847–851.

37. Leibowitz, S. F., Brain neuropeptide Y: an integrator of endocrine, metabolic and behavioral processes. Brain Research Bulletin., 1991. 27: p. 333–337.

38. Billington, C. J., et al., Effects of intracerebroventricular injection of neuropeptide Y on energy metabolism. Am. J. Physiol., 1991. 260: p. R321–R327.

39. Billington, C. J., et al., Neuropeptide-Y in hypothalamic paraventricular nucleus—a center coordinating energy-metabolism. American Journal Of Physiology, 1994. 266(6): p. R1765–R1770.

40. Kalra, S. P., et al., Neuropeptide Y secretion increases in the paraventricular nucleus in association with increased appetite for food. Proc. Natl. Acad. Sci. USA, 1991. 88: p. 10931–10935.

41. Beck, B., et al., Rapid and localized alterations of neuropeptide Y in discrete hypothalamic nuclei with feeding status. Brain Res, 1990. 528(2): p. 245–9.

42. Brady, L. S., et al., Altered expression of hypothalamic neuropeptide mRNAs in food-restricted and food-deprived rats. Neuroendocrinology, 1990. 52(5): p.441–7.

43. Calza, L., et al., Increase of neuropeptide Y-like immunoreactivity in the paraventricular nucleus of fasting rats. Neurosci Lett, 1989. 104(1–2): p. 99–104.

44. Sahu, A., P. S. Kalra, and S. P. Kalra, Food deprivation and ingestion induce reciprocal changes in neuropeptide Y concentrations in the paraventricular nucleus. Peptides, 1988. 9(1): p. 83–6.

45. Abe, M., et al., Increased neuropeptide Y content in the arcuato-paraventricular hypothalamic neuronal system in both insulin-dependent and non-insulin-dependent diabetic rats. Brain Res, 1991. 539(2): p. 223–7.

46. Sahu, A., et al., Neuropeptide-Y concentration in microdissected hypothalamic regions and in vitro release from the medial basal hypothalamus-preoptic area of streptozotocin-diabetic rats with and without insulin substitution therapy. Endocrinology, 1990. 126(1): p. 192–8.

47. White, J. D., et al., Increased hypothalamic content of preproneuropeptide-Y messenger ribonucleic acid in streptozotocin-diabetic rats. Endocrinology, 1990. 126(2): p. 765–72.

48. Williams, G., et al., Increased hypothalamic neuropeptide Y concentrations in diabetic rat. Diabetes, 1988. 37(6): p. 763–72.

49. Williams, G., et al., Increased neuropeptide Y concentrations in specific hypothalamic regions of streptozocin-induced diabetic rats. Diabetes, 1989. 38(3): p. 321–7.

50. Beck, B., et al., Hypothalamic neuropeptide Y (NPY) in obese Zucker rats: implications in feeding and sexual behaviors. Physiol Behav, 1990. 47(3): p. 449–53.

51. Sanacora, G., et al., Increased hypothalamic content of preproneuropeptide Y messenger ribonucleic acid in genetically obese Zucker rats and its regulation byfood deprivation. Endocrinology, 1990. 127(2): p. 730–7.

52. Wahlestedt, C., R. Ekman, and E. Widerlov, Neuropeptide Y (NPY) and the central nervous system: distribution effects and possible relationship to neurological and psychiatric disorders. Prog Neuropsychophannacol Biol Psychiatry, 1989. 13(1-2): p. 31–54.
53. Larhammar, D., et al., Cloning andfunctional expression of a human neuropeptide Y/peptide YY receptor of the Y1-type. J. Biol. Chem., 1992. 267: p. 10935–10938.
54. Sheikh, S. P., et al., Localization of Y1 receptors for NPY and PYY on vascular smooth muscle cells in rat pancreas. Am J Physiol, 1991. 260: p. G250–G257.
55. Wahlestedt, C., N. Yanaihara, and R. Hakanson, Evidence for different pre- and post-junctional receptors for neuropeptide Y and related peptides. Regul Pept, 1986. 13(3-4): p. 307–18.
56. Jorgensen, J. C., J. Fuhlendorff, and T. W. Schwartz, Structure-function studies on neuropeptide Y and pancreatic polypeptide-evidence for two PP-fold receptors in vas deferens. Eur J Pharmacol, 1990. 186(1): p. 105–14.
57. Cox, H. M. and J. L. Krstenansky, The effects of selective amino acid substitution upon neuropeptide Y antisecretory potency in rat jejunum mucosa. Peptides, 1991. 12(2): p. 323–7.
58. Aicher, S. A., et al., Receptor-selective analogs demonstrate NPY/PYY receptor heterogeneity in rat brain. Neurosci Lett, 1991. 130(1): p. 32–6.
59. Balasubramaniam, A., et al., Characterization of neuropeptide Y binding sites in rat cardiac ventricular membranes. Peptides, 1990. 11(3): p. 545–50.
60. Li, X. J., et al., Cloning, functional expression, and developmental regulation of a neuropeptide Y receptor from Drosophila melanogaster. J Biol Chem, 1992. 267(1): p. 9–12.
61. Roman, F. J., et al., Neuropeptide Y and peptide YY interact with rat brain sigma and PCP binding sites. Eur J Phannacol, 1989. 174(2–3): p. 301–2.
62. Schwartz, T. W., S. P. Sheikh, and M. M. O'Hare, Receptors on phaeochromocytoma cells for two members of the PP-foldfamily-NPY and PP. Febs Lett, 1987. 225(1-2): p. 209–14.
63. Schwartz, T. W., et al., Signal epitopes in the three-dimensional structure of neuropeptide Y. Interaction with Y1, Y2, and pancreatic polypeptide receptors. Ann N Y Acad Sci, 1990. 611(35): p. 35–47.
64. Wahlestedt, C., et al., Modulation of anxiety and neuropeptide Y-Y1 receptors by antisense oligodeoxynucleotides. Science, 1993. 259: p. 528–531.
65. Jolicoeur, F. B., et al., In vivo structure activity study supports the existence of heterogeneous neuropeptide Y receptors. Brain Res Bull, 1991. 26(2): p. 309–11.
66. Leibowitz, S. F. and J. T. Alexander, Analysis of neuropeptide Y-induced feeding: dissociation of Y1 and Y2 receptor effects on natural meal patterns. Peptides, 1991.12 (6): p. 1251–60.
67. Inui, A., et al., Characterization of peptide YY receptors in the brain. Endocrinology, 1989. 124(1): p. 402–9.
68. Boublik, J., et al., Neuropeptide Y and neuropeptide Y18–36. Structural and biological characterization. Int J Pept Protein Res, 1989. 33(1): p. 11–5.
69. Eva, C., et al., Molecular cloning of a novel G protein-coupled receptor that may belong to the neuropeptide receptor family. FEBS Lett., 1990. 271: p. 81–84.
70. Herzog, H., et al., Cloned human neuropeptide Y receptor couples to two different second messenger systems. Proc Natl Acad Sci U S A, 1992. 89: p. 5794–5798.
71. Strader, C. D., I. S. Sigal, and R. A. Dixon, Structural basis of beta-adrenergic receptor function. FASEB-J, 1989. 3(7): p. 1825–1832.
72. Bard, J. A., Walker, M. W., Brancheck, T., Weinshank, R. DNA encoding a human neuropeptide Y/peptide YY/pancreatic polypeptide receptor (Y4) and uses thereof. PCT International Application Publication No. WO 95/17906, published Jul. 6, 1995.
73. Gerald, C., Walker, M. W., Branchek, T., and Weinshank, R. Nucleic acid encoding Neuropeptide Y/Peptide YY (Y2 (receptors and uses thereof. PCT International Application Publication No. W095/21245, published Aug. 10, 1995.
74. Rose, P. A. et al., Cloning and functional expression of a cDNA encoding the human type 2 neuropeptide Y receptor. J. Biol. Chem., 270:22661–22664.

SUMMARY OF THE INVENTION

Modified neuropeptide Y receptors having deletions, replacements or additions in the third intracellular domain are identified and methods of making the modified receptors are provided. The invention includes the modified receptors, assays employing the modified receptors, cells expressing the modified receptors, compounds identified through the use of the modified receptors, including modulators of the receptors, and the use of the compounds to treat conditions, including obesity, diabetes, anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases.

BRIEF DESCRIPTION OF THE DRAWINGS

FIG. 3 shows the amino acid sequence of the human NPY1 receptor subtype aligned with that of the hamster $\beta_2$-adrenergic receptor.

DETAILED DESCRIPTION OF THE INVENTION

Modified neuropeptide Y receptors having deletions, replacements or additions in the third intracellular domain are identified and methods of making the modified receptors are provided. The invention includes the modified receptors, assays employing the modified receptors, cells expressing the modified receptors, compounds identified through the use of the modified receptors, including modulators of the receptors, and the use of the compounds to treat conditions, including obesity, diabetes, anxiety, hypertension, cocaine withdrawal, congestive heart failure, memory enhancement, cardiac and cerebral vasospasm, pheochroniocytoma and ganglioneuroblastoma, and Huntington's, Alzheimer's and Parkinson's diseases. Modulators, as described herein, include but are not limited to agonists, antagonists, suppressors and inducers.

Neuropeptide Y receptors belong to a class of receptors known as "G-protein coupled receptors." The term "G-protein coupled receptor" refers to any receptor protein that mediates its endogenous signal transduction through activation of one or more guanine nucleotide binding regulatory proteins (G-proteins). These receptors share common structural features, including seven hydrophobic transmembrane domains. G-protein coupled receptors include receptors that bind to small biogenic amines, including but not limited to beta-adrenergic receptors (βAR), alpha-adrenergic receptors (αAR) and muscarinic receptors, as well as receptors whose endogenous ligands are peptides, such as neurokinin, neuropeptide Y and glucagon receptors. Examples of βAR include beta-1, beta-2, and beta-3 adrenergic receptors.

G-protein coupled receptors are cell surface proteins that mediate the responses of a cell to a variety of environmental signals. Upon binding an agonist, the receptor interacts with one or more specific G proteins, which in turn regulate the activities of specific effector proteins. By this means, activation of G-protein coupled receptors amplifies the effects of the environmental signal and initiates a cascade of intracellular events that ultimately leads to defined cellular responses. G-protein coupled receptors function as a complex information processing network within the plasma membrane of the cell, acting to coordinate a cell's response to multiple environmental signals.

Figure 1:
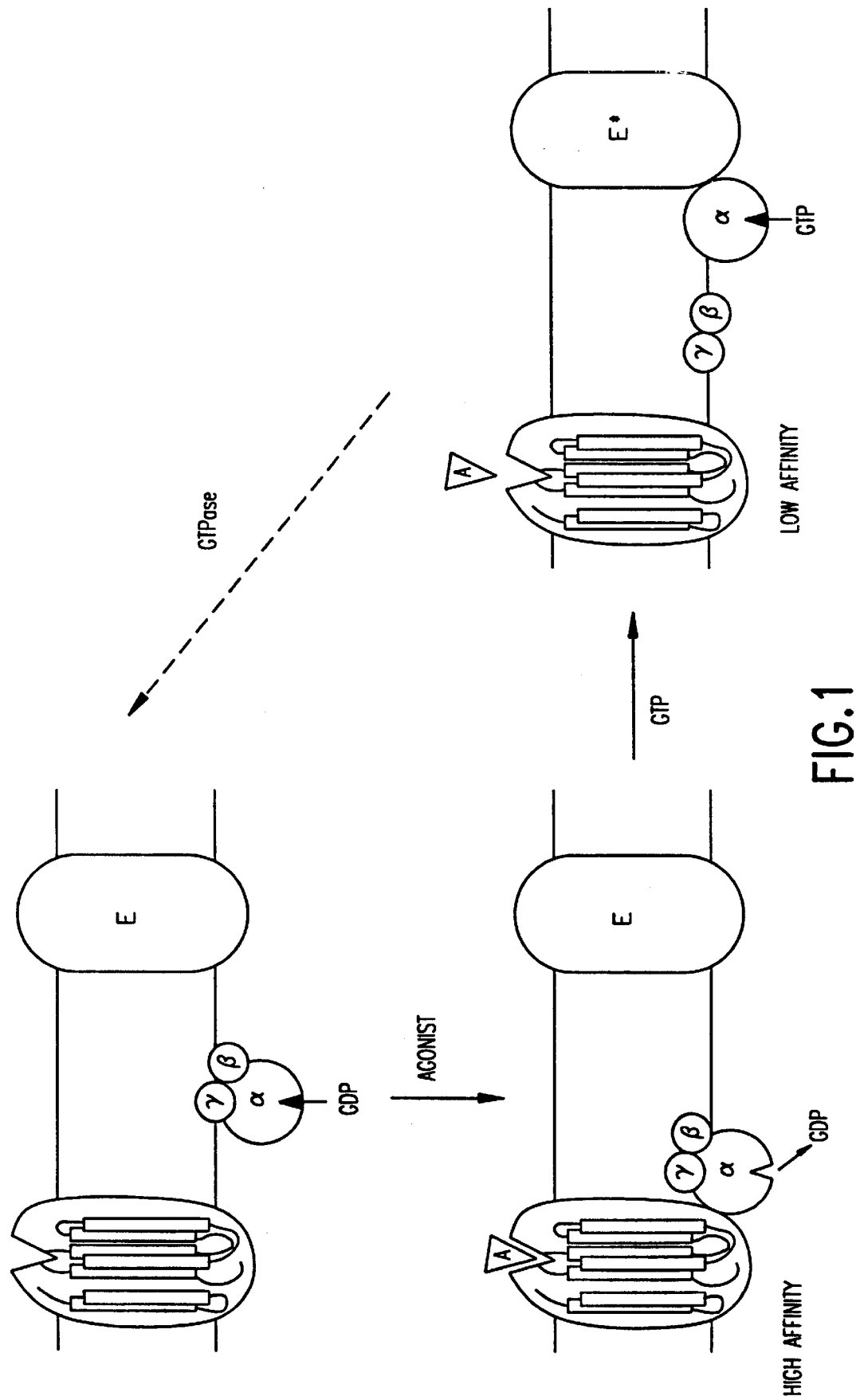
FIG. 1. Schematic diagram of G-protein signal transduction system. The receptor is shown as a seven-helical bundle. $\alpha$, $\beta$, and $\gamma$ indicate the three subunits of the G protein. E indicates an effector enzyme, such as adenylyl cyclase. The agonist (A) binding with high affinity to the receptor-G protein complex and with low affinity to the receptor alone is shown.
Figure 2A:
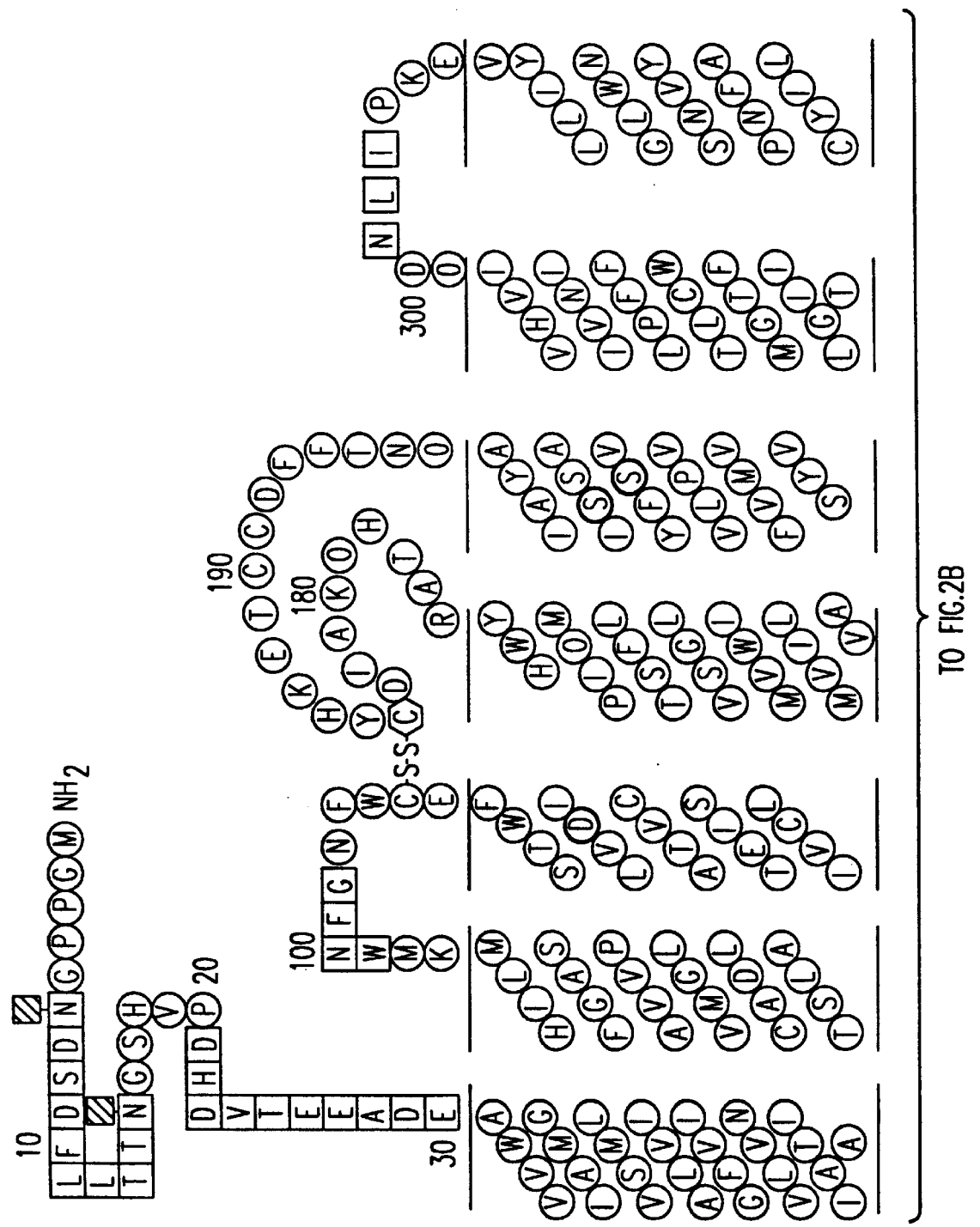
FIGS. 2A and 2B. Schematic diagram of the hamster $\beta_2$ adrenergic receptor. The third intracellular loop comprises residues 221–273. The proximal and distal segments of this loop are drawn in cylinders.
Figure 2B:
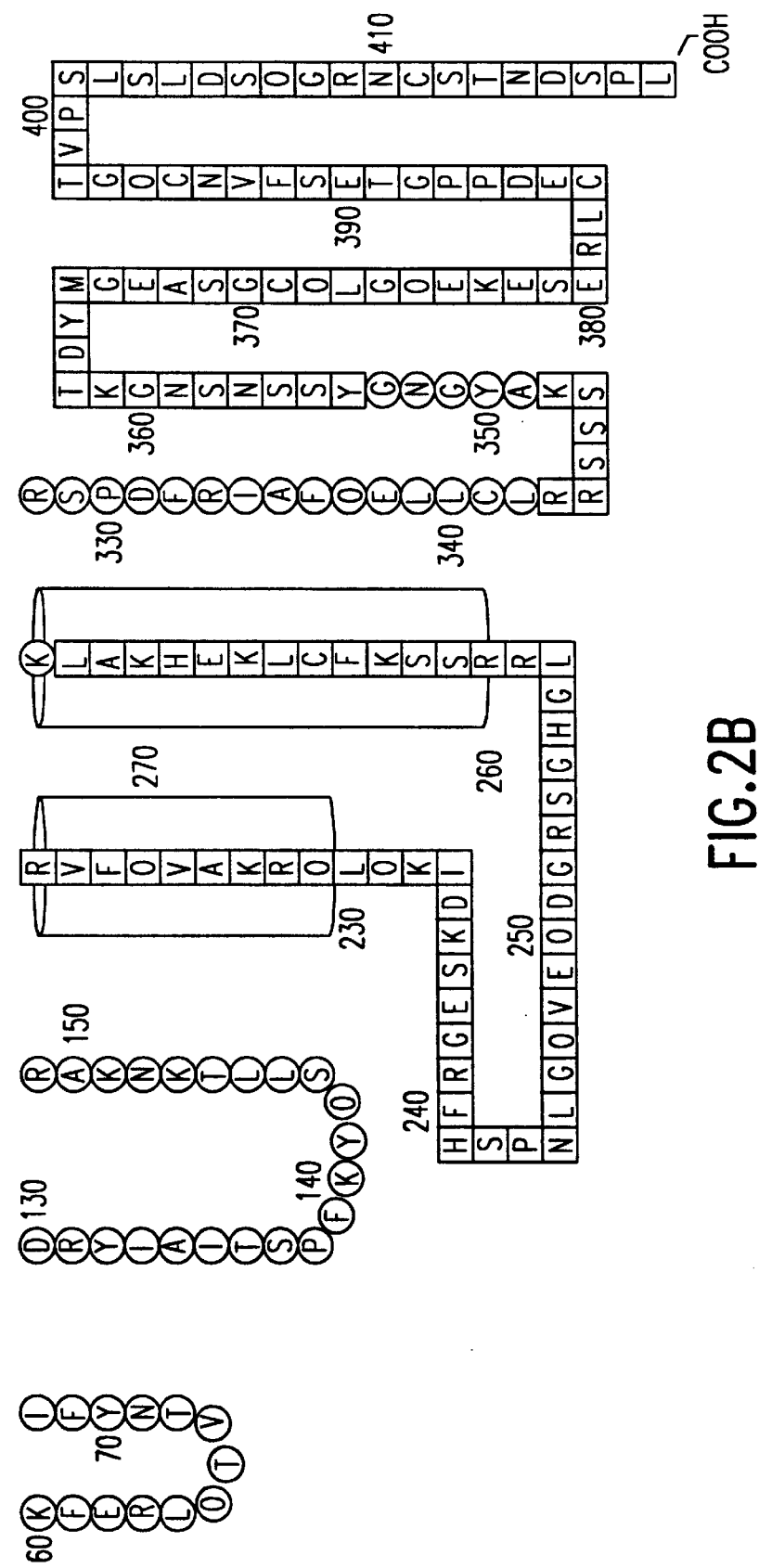

G-protein coupled receptors are characterized by the ability of agonists to promote the formation of a high affinity ternary complex between the agonist, the receptor and the G-protein (FIG. 1). The α-subunit of the G protein contains a guanine nucleotide binding site which, in the high affinity ternary [G protein-receptor-agonist] complex, is occupied by GDP. In the presence of physiological concentrations of GTP, the GDP molecule in the guanine nucleotide binding site of the G protein is displaced by a GTP molecule. The binding of GTP dissociates the α subunit of the G protein from its β and γ subunits and from the receptor, thereby activating the G-protein to stimulate downstream effectors (adenylyl cyclase in the case of the β-adrenergic receptor (βPAR)) and propagating the intracellular signal. Thus, the ternary complex is transient in the presence of physiological concentrations of GTP. Because the affinity of the agonist for the receptor-G protein complex is higher than its affinity for the uncomplexed receptor, one consequence of the destabilization of the ternary complex is a reduction in the affinity of the receptor for the agonist. Thus, the affinity of agonists for G-protein coupled receptors is a function of the efficiency with which the receptor is coupled to the G-protein. In contrast, antagonists bind with the same affinity to the receptor in the presence or absence of G-protein coupling.

The observation that agonist affinity can be reduced by conditions under which a receptor is not optimally coupled to its G-protein has important implications for the identification of agonists of G-protein coupled receptors, particularly identification based on ligand binding. If a receptor is not optimally coupled to the G-protein under the conditions of binding assays, an agonist will bind to the receptor with relatively low affinity. Thus, a screen that relies on a binding assay based on displacement of a radiolabeled ligand, although attractive for its ease and the potential for high throughput, poses the risk that a promising partial agonist might be overlooked because the agonist would bind predominantly to the low affinity state of the receptor, and thus would have low affinity in the binding assay. Consequently, functional assays are frequently used to screen for agonists of G-protein coupled receptors. However, functional assays (ranging from ex vivo muscle contraction assays to determination of second messenger levels in cells expressing exogenous cloned G-protein coupled receptors) are tedious and more time-consuming than ligand binding assays, and hence are not readily adapted to high-throughput screens. Because the modified receptors of the present invention bind agonists with high affinity in the presence or absence of the G-protein, they can be used in high throughput radioligand binding assays to screen for high affinity ligands, regardless of whether the ligands are agonists or antagonists.

G-protein coupled receptors consist of seven hydrophobic domains connecting eight hydrophilic domains. The hydrophobicity or hydrophilicity of the domains may be determined by standard hydropathy profiles, such as Kyte-Doolittle analysis (Kyte, J. and Doolittle, R. J. F. *J. Mol. Biol.* 157: 105 (1982)). The receptors are thought to be oriented in the plasma membrane of the cell such that the N-terminus of the receptor faces the extracellular space and the C-terminus of the receptor faces the cytoplasm, so that each of the hydrophobic domains crosses the plasma membrane. The receptors have been modeled and the putative boundaries of the extracellular, transmembrane and intracellular domains are generally agreed (for a review, see Baldwin, EMBO J. 12:1693, 1993). In general, the transmembrane domains are comprised of stretches of 20–25 amino acids in which most of the amino acid residues have hydrophobic side chains (including cysteine, methionine, phenylalanine, tyrosine, tryptophan, proline, glycine, alanine, valine, leucine, isoleucine), whereas the intracellular and extracellular loops are defined by contiguous stretches of several amino acids that have hydrophilic or polar side chains (including aspartate, glutamate, asparagine, glutamine, serine, threonine, histidine, lysine, and arginine). Polar amino acids, especially uncharged ones (such as serine, threonine, asparagine, and glutamine) are found in both transmembrane and extramembrane regions.

The extramembrane regions are characterized by contiguous stretches of three or more hydrophilic residues. In contrast, hydrophilic residues are found only in groups of 1–2, surrounded by hydrophobic residues, in the transmembrane domain. Thus, the transmembrane and extramembrane regions can be identified by the number of contiguous hydrophilic or hydrophobic amino acids in the primary sequence of the receptor, in addition to the constraints on the length of the hydrophobic segments given above. The boundaries between the transmembrane and extramembrane regions are often defined by the presence of charged or polar residues at the beginning or end of a stretch of hydrophobic amino acids. The locations of the mutations in the receptors of the present invention are described on the basis of these models and can be specifically defined by the specific amino acid numbers of the residues being mutated.

By these criteria, the third intracellular loop is defined as the hydrophilic loop connecting the hydrophobic, putative transmembrane domains V and VI. For example, in hamster $\beta_2$ adrenergic receptor, the third intracellular loop would refer to amino acids 221 through 273. In accordance with the principles described above, the beginning of this loop is defined by the presence of Arg221 (a charged residue at the end of the hydrophobic stretch of residues 198–220) and $Lys_{273}$ (a charged residue at the beginning of the hydrophobic stretch of residues 274–298). In the human NPY1 receptor (PCT International Application Publication Nos. WO93/09227 published May 13, 1993 and WO93/24515 published Dec. 9, 1993, the contents of both of which are hereby incorporated by reference), the third intracellular loop refers to amino acids #233–260 (FIG. 3). In accordance with the principles described above, the beginning of this loop is defined by the presence of Lys233 (a charged residue at the end of the long stretch of hydrophobic residues comprising helix 5) and Arg260 (a charged residue at the beginning of the long stretch of hydrophobic residues comprising helix 6). In the rat NPY1 receptor, the third intracellular loop refers to amino acids #232–259 (Eva, C., et al., FEBS Lett. 271:81, 1990). In accordance with the principles described above, the beginning of this loop is defined by the presence of Lys232 (a charged residue at the end of the long stretch of hydrophobic residues comprising helix 5) and Arg259 (a charged residue at the beginning of the long stretch of hydrophobic residues comprising helix 6). In the human and rat NPY2 receptors, the third intracellular loop refers to amino acids #241–268 (Gerald, C., et al., PCT International Application Publication No. W095/21245, the contents of which are hereby incorporated by reference). In accordance with the principles described above, the beginning of this loop is defined by the presence of Arg241 (a charged residue at the end of the long stretch of hydrophobic residues comprising helix 5) and Lys268 (a charged residue at the beginning of the long stretch of hydrophobic residues comprising helix 6). In the human NPY4 receptor, the third intracellular loop refers to amino acids #236–263 (Bard, J. A., et al., PCT International Application Publication No. W095/17906, the contents of which are hereby incorporated by reference). In accordance with the principles described above, the beginning of this loop is defined by the presence of Arg236 (a charged residue at the end of the long stretch of hydrophobic residues comprising helix 5) and Gln263 (a polar residue at the beginning of the long stretch of hydrophobic residues comprising helix 6). In the rat NPY4 receptor, the third intracellular loop refers to amino acids #236–263 (Bard, J. A., et al., PCT International Application Publication No. W095/17906). In accordance with the principles described above, the beginning of this loop is defined by the presence of Arg236 (a charged residue at the end of the long stretch of hydrophobic residues comprising helix 5) and Arg263 (a charged residue at the beginning of the long stretch of hydrophobic residues comprising helix 6).

The present invention pertains to modified neuropeptide Y receptors having deletions, replacements or additions in the third intracellular domain. Methods of designing and making modified receptors are provided. The modified receptors are uncoupled from or are poorly coupled to their respective neuropeptides. However, these modified receptors bind agonists with high affinity in the absence of G protein coupling. Because of their high intrinsic affinity for agonists, these modified receptors may be used in high throughput binding assays to identify compounds that bind to the receptor with high affinity, regardless of whether these compounds are agonists or antagonists. The invention includes the DNA encoding the modified receptors, the modified receptors, assays employing the modified receptors, cells expressing the modified receptors, substances identified through the use of the modified receptors including specific modulators of the modified receptors, and the use of these substances in treating diseases, including obesity, diabetes, cardiovascular, and neurological disorders. Modulators identified in this process are useful as therapeutic agents. Modulators, as described herein, include but are not limited to agonists, antagonists, suppressors and inducers.

Modified receptors may include genetic variants, both natural and induced. Induced modified receptors may be derived by a variety of methods, including but not limited to, site-directed mutagenesis. Techniques for nucleic acid and protein manipulation are well-known in the art and are described generally in Methods in Enzymology and in Sambrook et al., Molecular Cloning: A Laboratory Manual, Cold Spring Harbor Laboratory (1989).

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of a modified receptor is a compound that possesses a biological activity (either functional or structural) that is substantially similar to the biological activity of the modified receptor. The term "functional derivative" is intended to include the "fragments," "variants," "degenerate variants," "analogs" and "homologues" or to "chemical derivatives" of modified receptors. The term "fragment" is meant to refer to any polypeptide subset of modified receptors. The term "variant" is meant to refer to a molecule substantially similar in structure and function to either the entire modified receptor molecule or to a fragment thereof. A molecule is "substantially similar" to a modified receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire modified receptor molecule or to a fragment thereof.

"Substantial homology" or "substantial similarity", when referring to nucleic acids means that the segments or their complementary strands, when optimally aligned and compared, are identical with appropriate nucleotide insertions or deletions, in at least 50% of the nucleotides. Alternatively, substantial homology exists when the segments will hybridize to a strand or its complement.

The nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

Nucleic acid compositions of this invention may be derived from genomic DNA or cDNA, prepared by synthesis or by a combination of techniques.

The natural or synthetic nucleic acids encoding the modified G-coupled protein receptors of the present invention may be incorporated into expression vectors. Usually the expression vectors incorporating the modified receptors will be suitable for replication in a host. Examples of acceptable hosts include, but are not limited to, prokaryotic and eukaryotic cells.

The phrase "recombinant expression system" as used herein means a substantially homogenous culture of suitable host organisms that stably carry a recombinant expression vector. Examples of suitable hosts include, but are not limited to, bacteria, yeast, fungi, insect cells, plant cells and mammalian cells. Generally, cells of the expression system are the progeny of a single ancestral transformed cell.

The cloned modified receptor DNA obtained through the methods described herein may be recombinantly expressed by molecular cloning into an expression vector containing a suitable promoter and other appropriate transcription regulatory elements, and transferred into prokaryotic or eukaryotic host cells to produce recombinant modified receptor. Techniques for such manipulations are fully described in Sambrook, J., et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungi or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant modified receptor in mammalian cells. Commercially available mammalian expression vectors which may be suitable for recombinant modified receptor expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565), pCI-neo (Promega).

A variety of bacterial expression vectors may be used to express recombinant modified receptor in bacterial cells. Commercially available bacterial expression vectors which may be suitable for recombinant modified receptor expression include, but are not limited to pET11a (Novagen), lambda gt11 (Invitrogen), pcDNAII (Invitrogen), pKK223-3 (Pharmacia).

A variety of fungal cell expression vectors may be used to express recombinant modified receptor in fungal cells. Commercially available fungal cell expression vectors which may be suitable for recombinant modified receptor expression include but are not limited to pYES2 (Invitrogen), Pichia expression vector (Invitrogen).

A variety of insect cell expression vectors may be used to express recombinant receptor in insect cells. Commercially available insect cell expression vectors which may be suitable for recombinant expression of modified receptor include but are not limited to pBlue Bac III (Invitrogen).

An expression vector containing DNA encoding modified receptor may be used for expression of modified receptor in a recombinant host cell. Recombinant host cells may be prokaryotic or eukaryotic, including but not limited to bacteria such as E. coli. fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce modified receptor protein. Identification of modified receptor expressing host cell clones may be done by several means, including but not limited to immunological reactivity with anti-modified receptor antibodies.

Expression of modified receptor DNA may also be performed using in vitro produced synthetic mRNA or native mRNA. Synthetic mRNA or mRNA isolated from modified receptor producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

The term "substantial homology", when referring to polypeptides, indicates that the polypeptide or protein in question exhibits at least about 30% homology with the naturally occurring protein in question, usually at least about 40% homology.

The modified receptors may be expressed in an appropriate host cell and used to discover compounds that affect the modified receptor. Preferably, the modified receptors are expressed in a mammalian cell line, including but not limited to, COS-7, CHO or L cells, or an insect cell line, including but not limited to, Sf9 and Sf21, and may be used to discover ligands that bind to the receptor and alter or stimulate its function. The modified receptors may also be produced in bacterial, fungal or yeast expression systems.

The expression of the modified receptor may be detected by use of a radiolabeled ligand specific for the receptor. For example, for the $\beta_2$ adrenergic receptor, such a ligand may be $^{125}$I-iodocyanopindolol ($^{125}$I-CYP). For the NPY receptor, such a ligand may be $^{125}$I-NPY, $^{125}$I-Peptide YY (PYY) or $^{125}$I-Pancreatic polypeptide.

The specificity of binding of compounds showing affinity for the modified receptors is shown by measuring the affinity of the compounds for cells transfected with the cloned modified receptor or for membranes from these cells. Expression of the cloned modified receptor and screening for compounds that inhibit the binding of radiolabeled ligand to these cells provides a rational way for rapid selection of compounds with high affinity for the receptor. These compounds may be agonists or antagonists of the receptor. Because the modified receptor does not couple well to G proteins, the agonist activity of these compounds is best assessed by using the wild-type receptor, either natively expressed in tissues or cloned and exogenously expressed.

Once the modified receptor is cloned and expressed in a mammalian cell line, such as COS-7 cells or CHO cells, the recombinant modified receptor is in a well-characterized environment. The membranes from the recombinant cells expressing the modified receptor are then isolated according to methods known in the art. The isolated membranes may be used in a variety of membrane-based receptor binding assays. Because the modified receptor has a high affinity for agonists, ligands (either agonists or antagonists) may be identified by standard radioligand binding assays. These assays will measure the intrinsic affinity of the ligand for the receptor.

The present invention provides methods of generating modified NPY receptors. Such methods generally comprise the deletion of at least one nucleotide from the third intracellular domain of the receptor. Additional methods include, but are not limited to, enzymatic or chemical removal of amino acids from the third intracellular domain of the receptor. One method of generating modified NPY receptors comprises:

(a) isolating DNA encoding an NPY receptor;

(b) altering the DNA of step (a) by deleting at least one nucleotide from DNA encoding the third intracellular domain of the NPY receptor or disrupting the amphipathic helix at the N- or C-terminus of the third intracellular domain by replacement with nucleotides or addition of nucleotides coding for non-helical protein sequence;

(c) isolating the altered DNA;

(d) expressing the altered DNA; and (e) recovering the modified NPY receptor. The third intracellular domain of a G-protein coupled receptor is located between the fifth and sixth hydrophobic transmembrane domains of the receptor.

The present invention provides methods of identifying compounds that bind to modified NPY receptors. Methods of identifying compounds are exemplified by an assay, comprising:

a) cloning a neuropeptide Y receptor, b) altering the DNA sequence encoding the third intracellular domain of the cloned receptor, c) splicing the altered receptor into an expression vector to produce a construct such that the altered receptor is operably linked to transcription and translation signals sufficient to induce expression of the receptor upon introduction of the construct into a prokaryotic or eukaryotic cell;

d) introducing the construct into a prokaryotic or eukaryotic cell which does not express the altered receptor in the absence of the introduced construct; and e) incubating cells or membranes isolated from cells produced in step c with a quantifiable compound known to bind to the receptors, and subsequently adding test compounds at a range of concentrations so as to compete the quantifiable compound from the receptor, such that an $IC_{50}$ for the test compound is obtained as the concentration of test compound at which 50% of the quantifiable compound becomes displaced from the receptor.

The present invention is also directed to methods for screening for compounds which modulate the expression of DNA or RNA encoding modified receptors or which modulate the function of modified receptor protein. Compounds which modulate these activities may be DNA, RNA, peptides, proteins, or non-proteinaceous organic molecules. Compounds may modulate by increasing or attenuating the expression of DNA or RNA encoding modified receptor, or the function of modified receptor protein. Compounds that modulate the expression of DNA or RNA encoding modified receptor or the function of modified receptor protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing modified receptor DNA, antibodies to modified receptor, or modified receptor protein may be prepared. Such kits are used to detect DNA which hybridizes to modified receptor DNA or to detect the presence of modified receptor protein or peptide fragments in a sample. Such characterization is useful for a variety of purposes including but not limited to forensic, taxonomic or epidemiological studies.

The DNA molecules, RNA molecules, recombinant protein and antibodies of the present invention may be used to screen and measure levels of modified receptor DNA, modified receptor RNA or modified receptor protein. The recombinant proteins, DNA molecules, RNA molecules and antibodies lend themselves to the formulation of kits suitable for the detection and typing of modified receptor. Such a kit would comprise a compartmentalized carrier suitable to hold in close confinement at least one container. The carrier would further comprise reagents such as recombinant modified receptor protein or anti-modified receptor antibodies suitable for detecting modified receptor. The carrier may also contain a means for detection such as labeled antigen or enzyme substrates or the like.

Pharmaceutically useful compositions comprising modulators of modified receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The modified G-protein coupled receptors of the present invention are exemplified herein by the neuropeptide Y receptors.

Deletion mutagenesis of the $\beta_2$-adrenergic receptor has shown that none of the hydrophobic clusters of amino acids (the putative transmembrane helices) could be deleted without substantial loss of binding. In contrast, most of the connecting loops could be deleted without affecting the ligand binding properties of the receptor. This indicates that these hydrophilic loops are not required for ligand binding to the receptor, suggesting that the ligand binding pocket is located predominantly within the transmembrane domain of the protein (Strader, et al. *FASEB J*.3: 182–183 (1989)). Deletions in the connecting loops that were large enough to encompass the entire loop led to steric problems, resulting in incorrect processing of the protein (Dixon, et al. *EMBO J*. 6: 3269–3275 (1987)). Certain connecting loop deletion mutations, however, led to loss of functional activation of adenylyl cyclase by the receptor. For example, deletion of the carboxy terminal region of the third intracellular loop attenuated the ability of the receptor to activate adenylyl cyclase, and deletion of the amino terminal portion of this loop abolished adenylyl cyclase activation (Strader, et al. *J. Biol. Chem.* 262: 16439–16443 (1987)). Moreover, the agonist binding isotherms for these modified receptors displayed a single anity site, suggesting altered G protein interactions. Since these modified receptors also retain their functional activation of $Na^+$-$H^+$ exchange, which is mediated through a different G protein (Barber, et al. *Mol. Pharm.* 41: 1056–1060 (1992)), the deletions appear not to result in gross structural perturbations of the receptor, suggesting that the changes seen in adenylyl cyclase activation are due to alteration of a specific G protein interaction. Subsequent amino acid replacements in the third intracellular loop confirmed the role of this region in G protein interaction (Cheung, et al. *Mol. Pharm.* 41: 1061–1065 (1992)).

Modified NPY1 receptors lacking between 6 and 12 amino acids in the N terminal portion of the third intracellular loop (connecting transmembrane helices 5 and 6) may be synthesized. The bottom of transmembrane helix 5 is defined by the presence of a charged amino acid (human NPY1 Lys233, rat NPY1 Lys232) at the end of a series of hydrophobic amino acids. The modified receptors include the deletion of 6–12 residues following Lys233 (human) or Lys232 (rat) (i.e., $I^{234}$YIRLKRRNNMM; Seq. I.D. No. 1). Alternatively, this sequence could be disrupted by deletion of one or more of the charged residues (ie., K238, R239 or R240), or replacement of such residues with alanine or a helix-disrupting residue such as proline.

A second group of modified NPY1 receptors encompass the deletion of 6–13 residues at the C terminal end of the third intracellular loop of the receptor. The C terminus of this loop is defined by the bottom of helix 6, defined by the presence of the charged residue Arg260 (human NPY1) or Arg259 (rat NPY1) preceding a stretch of hydrophobic amino acids. The modified receptors of this group have deletions of 6–13 residues preceding Arg 260 in human NPY1 (i.e., $KMRDNKYRSSETK^{259}$; Seq. I.D. No. 2) and proceeding Arg259 in rat NPY1 (i.e., KIRDSKYRS-$SETK^{258}$; Seq. I.D. No. 4). Alternatively, this sequence could be disrupted by deletion of one or more of the charged residues (ie., R249, D250, K252), or replacement of such residues with alanine or a helix-disrupting residue such as proline.

Modified NPY2 receptors lacking between 6 and 12 amino acids in the N terminal portion of the third intracellular loop (connecting transmembrane helices 5 and 6) may be synthesized. The bottom of transmembrane helix 5 is defined by the presence of a charged amino acid (Arg241 in rat and human) at the end of a series of hydrophobic amino acids. The modified receptors include the deletion of 6–12 residues following Arg241 (i.e., $I^{242}$WSKLKNHVSPG; Seq. I.D. No. 5). Alternatively, this sequence could be disrupted by deletion of one or more of the charged residues (ie., K244, K246 or H248), or replacement of such residues with alanine or a helix-disrupting residue such as proline.

A second group of modified NPY2 receptors encompass the deletion of 6–13 residues at the C terminal end of the third intracellular loop of the receptor. The C terminus of this loop is defined by the bottom of helix 6, defined by the presence of the charged residue (Lys268 in human and rat) preceding a stretch of hydrophobic amino acids. The modified receptors of this group have deletions of 6–13 residues preceding Lys268 in human NPY2 (i.e., ANDHYHQR-$RQKTT^{267}$; Seq. I.D. No. 6) and proceeding Lys268 in rat NPY2 (i.e., $AASDHYHQRRHKTT^{267}$; Seq. I.D. No. 7). Alternatively, this sequence could be disrupted by deletion of one or more of the charged residues (ie., D257, H258, H260, R262, R263, H264, K265), or replacement of such residues with alanine or a helix-disrupting residue such as proline.

Modified NPY4 receptors lacking between 6 and 12 amino acids in the N terminal portion of the third intracellular loop (connecting transmembrane helices 5 and 6) may be synthesized. The bottom of transmembrane helix 5 is defined by the presence of a charged amino acid (Arg236 in rat and human) at the end of a series of hydrophobic amino acids. The modified receptors include the deletion of 6–12 residues following Arg236 (i.e., $I^{237}$YRRLQRQGRVF in human NPY4 (Seq. I.D. No. 8) and $I^{237}$YQRLQRQRRAF in rat NPY4 (Seq. I.D. No. 9)). Alternatively, this sequence could be disrupted by deletion of one or more of the charged residues (ie., R238, R239, R242, R245), or replacement of such residues with alanine or a helix-disrupting residue such as proline.

A second group of modified NPY4 receptors encompass the deletion of 6–13 residues at the C terminal end of the third intracellular loop of the receptor. The C terminus of this loop is defined by the bottom of helix 6, defined by the presence of the charged residue (Gln263 in human and Arg263 in rat) preceding a stretch of hydrophobic amino acids. The modified receptors of this group have deletions of 6–13 residues preceding Gln263 in human NPY4 (i.e., HKGTYSLRAGHMK$^{263}$; Seq. I.D. No. 10) and proceeding Arg263 in rat NPY4 (i.e., HTHTCSSRVGQMK$^{263}$; Seq. I.D. No. 11). Alternatively, this sequence could be disrupted by deletion of one or more of the charged residues (ie., H251, K252, R258, H261 ), or replacement of such residues with alanine or a helix-disrupting residue such as proline.

Other modified receptors encompass the deletion of 6–13 residues at either the N or C terminal end of the third intracellular loop, or replacement of residues within this region, of other members of the family of NPY receptors. The N terminus of the third intracellular loop (connecting transmembrane helices 5 and 6) is defined by the presence of a charged or polar amino acid at the end of the fifth series of hydrophobic amino acids in the sequence of the receptor (helix 5). The C terminus of this loop is located at the bottom of helix 6, defined by the presence of a charged or polar residue preceding the sixth stretch of hydrophobic amino acids.

Other modified receptors encompass the addition of 5 to 10 residues at either the N or C terminal end of the third intracellular loop of the NPY1, 2 or 4 receptors such that the amphipathic nature of these regions is disrupted.

The following examples are provided to further define the invention without, however, limiting the invention to the particulars of the examples.

EXAMPLE 1

Deletion of 6–13 amino acids at the N-terminal portion of the third intracellular loop of the human Neuropeptide Y1 receptor Modified receptor is constructed by site-directed mutagenesis of the human neuropeptide Y1 receptor cNDA by standard molecular biological techniques.

The modified DNA sequence encodes a human neuropepide Y1 receptor lacking between 6 and 13 amino acid residues at the N-terminal portion of the third intracellular loop. The nucleotide sequence of the modified receptor is confirmed by DNA sequencing. As with modified $\beta_2$ receptors, the modified NPY receptor is designed so as to disrupt the proximal portion of the third intracellular loop, without affecting the adjacent fifth transmembrane helix. Thus, the charged amino acid that delineates the bottom of helix 5 (Lys233) is left intact in the modified receptor, while the six to thirteen amino acids which follow it are deleted. The size of the deletion in the present invention may vary from six to 13 amino acids in this region, beginning immediately after the charged residue at the bottom of transmembrane helix 5, for example D(234–241)NPY1 receptor.

EXAMPLE 2

Deletion of 6–13 amino acids at the C-terminal portion of the third intracellular loop of the human Neuropeptide Y1 receptor Modified human NPY1 receptor, lacking 13 residues at the C-terminal portion of the third intracellular loop (D(247–259)NPY1 receptor), is prepared by standard mutagenesis procedures. The nucleotide sequences of the modified receptors are confirmed by DNA sequencing. This modified human NPY1 receptor is designed so as to disrupt the distal portion of the third intracellular loop, without affecting the adjacent sixth transmembrane helix. Thus, the charged amino acid that defines the bottom of helix 6 (Lys260) is left intact, while the nearby proximal residues are deleted. The size of the deletion in the present invention may vary from six to 13 amino acids in this region, ending immediately before the charged residues at the bottom of helix 6.

EXAMPLE 3

Expression and characterization of the altered Neuropeptide Y1 receptor

COS-7 cells are transfected with the modified receptor cDNA subcloned into a eukaryotic expression vector such as the eukaryotic expression vector pcDNA I/neo (Invitrogen). Cells are harvested after incubation for about 60–72 h. Membranes containing the expressed receptor protein are prepared as described (C. D. Strader et al., *Proc. Natl. Acad. Sci. U.S.A.* 84, 4384–4388 (1987).

Binding reactions are performed in a final volume of 250 $\mu$l of buffer A (50 $\mu$M Tris, pH 7.4 containing 20 mM CaCl$_2$, 5 mM KCl, 0.2% bovine serum albumin, 10 $\mu$M phosphoramidon, 40 $\mu$g/ml bacitracin and 2 $\mu$g/ml leupeptin). $^{125}$I-NPY or $^{125}$I-PYY (0.1 nM) is incubated with membranes for 2 hr at 25° C. before filtration over GF/C filters presoaked in 0.1% polyethyleneimine. Filters are washed with ice cold buffer A before analysis of the bound radioactivity by $\gamma$ scintillation counting.

Membranes prepared from the COS-7 cells transfected with a vector containing either the wild type or the modified receptor cDNA specifically bind a radiolabeled neuropeptide Y receptor radioligand. The modified receptor is characterized by an absence of coupling to G proteins, an inability to mediate the activation of second messenger systems, and an increased affinity for agonists.

The modified neuropeptide Y receptor, when expressed in mammalian cells, does not stimulate G protein activation in response to the agonist NPY. In contrast, when the wild type receptor is expressed in the same cell line, activity is stimulated.

These modified receptors have increased affinity for agonists when compared to the wild type receptor. The wild type NPY1 receptor can be described pharmacologically by the relative potency of peptide ligands: neuropeptide Y=peptide YY>[Leu31Pro34]NPY>NPY[2–36]>>NPY[13–36], with the affinity of NPY in the range of 0.1–10 nM, and NPY [13–36] having an affinity in the $\mu$M range. The mutant receptor binds the agonists with the same relative order of potency. The high affinity of the agonist for the modified receptor is not affected by agents that uncouple the receptor from the G protein; such agents include the nonhydrolyzable GTP analog GppNHp, sodium fluoride, and the detergent digitonin. In contrast, the wild type receptor binds agonists with two affinity states: a high affinity state, indicative of binding to the receptor-G protein complex, and a low affinity state, reflecting binding to the uncoupled receptor alone. When the receptor is not optimally coupled to the G protein, a binding assay using the modified receptor will detect agonists with more sensitivity than will the identical binding assay using the wild-type receptor.

EXAMPLE 4

Screening Assay using modified Neuropeptide Y1 receptors

Transfected cells expressing recombinant modified receptor may be used to identify compounds that bind to the receptor with high affinity. This may be accomplished in a variety of ways, such as by incubating the test compound in a final volume of 0.25 ml of buffer A with membranes containing 5–7 pM of the modified neuropeptide Y receptor and 100 pM $^{125}$I-PYY or $^{125}$I-NPY for 2 hour at 25°. The reaction is stopped by filtration over GF/C glass fiber filters presoaked in 0.1% polyethyleneimine, washing with 3×5 ml of cold buffer A, and. counting the filters in a gamma counter to measure bound radioactivity. This assay will detect a compound that has a high intrinsic affinity for the receptor. Such compounds may be either agonists or antagonists.

EXAMPLE 5

Deletion of 6–13 amino acids at the N-terminal portion of the third intracellular loop of Neuropeptide Y receptor subtypes Modified NPY receptor subtypes (e.g., NPY2, NPY4) having deletions at the N terminal region of the third intracellular loop are constructed by site-directed mutagenesis of the neuropeptide Y receptor cDNA by standard molecular biological techniques.

The modified DNA sequence encodes a neuropepide Y receptor lacking between 6 and 13 amino acid residues at the N-terminal portion of the third intracellular loop. The nucleotide sequence of the modified receptor is confirmed by DNA sequencing. The modified NPY receptor is designed so as to disrupt the proximal portion of the third intracellular loop, without affecting the adjacent fifth transmembrane helix. Thus, the charged amino acid that delineates the bottom of helix 5 is left intact in the modified receptor, while the six to thirteen amino acids which follow it are deleted. The size of the deletion in the present invention may vary from six to 13 amino acids in this region, beginning immediately after the charged residue at the bottom of transmembrane helix 5.

EXAMPLE 6

Deletion of 6–13 amino acids at the C-terminal portion of the third intracellular loop of the Neuropeptide Y receptor Modified NPY receptor subtypes (e.g., NPY2, NPY4) having deletions at the C terminal region of the third intracellular loop are constructed by site-directed mutagenesis of the neuropeptide Y receptor cDNA by standard molecular biological techniques. The nucleotide sequences of the modified receptors are confirmed by DNA sequencing. These modified NPY receptors have disruptions in the distal portion of the third intracellular loop, without affecting the adjacent sixth transmembrane helix. Thus, the polar amino acid that defmes the bottom of helix 6 is left intact, while the nearby proximal residues are deleted. The size of the deletion in the present invention may vary from six to 13 amino acids in this region, ending immediately before the polar residues at the bottom of helix 6.

EXAMPLE 7

Expression and characterization of modified NPY Receptor

The modified receptor is subcloned into an expression vector such as pRC/CMV (Invitrogen,San Diego, Calif.) and expressed in mammalian cells by transfection. Approximately 72 hours after transfection, cells are harvested for radioligand binding assays.

For binding assays, the membranes are prepared by harvesting the cells in ice-cold lysis buffer (5 mg Tris, pH 7.4; 2 mM EDTA), followed by 15 min centrifugation at 38,000× g. The membrane pellet is then resuspended in buffer A. Equilibrium binding to the wild type or modified NPY receptor is performed in a final volume of 0.25 ml containing membranes, 100 pM $^{125}$I-PYY, and serial dilution of the competing ligands. Binding reactions are incubated for 2 hr at 25° C., and terminated by rapid filtration over GF/C filters pre-soaked in 0.1% polyethyleneimine. The radioactivity is quantified with a Packard gamma counter.

These modified receptors have increased affinity for agonists when compared to the wild type receptor. The wild type "atypical NPY1" or NPY4 receptor that mediates feeding behavior can be described pharmacologically by the high affinity of neuropeptide Y, peptide YY, NPY[2–36], and [Leu31Pro34]NPY, and the lower affinity of more truncated analogs NPY[13–36] and NPY [20–36], and structurally by its sequence homology (>45% at the DNA level) to the NPY1 receptor. The affinity of NPY for the atypical Y1 receptor subtype is in the range of 0.01–10 nM, and that for NPY[13–36] is in the 0.1–10 μM range. The mutant receptor binds the agonists with the same relative order of potency as the wild type receptor. The high affinity of the agonist for the modified receptor is not affected by agents that uncouple the receptor from the G protein; such agents include the non-hydrolyzable GTP analog GppNHp, sodium fluoride, and the detergent digitonin. In contrast, the wild type receptor binds agonists with two affinity states: a high affinity state, indicative of binding to the receptor-G protein complex, and a low affinity state, reflecting binding to the uncoupled receptor alone. When the receptor is not optimally coupled to the G protein, a binding assay using the modified receptor will detect agonists with more sensitivity than will the identical binding assay using the wild-type receptor. Other NPY receptor subtypes (NPY2, NPY3, and others) are also defined pharmacologically by the relative potencies of peptide ligands for these receptors and structurally by their sequence similarity to the NPY 1 receptor. Mutant receptors having deletions in the third intracellular loop have similar orders of potency as the corresponding wild type receptor, but with higher affinity than the wild type receptor in the absence of G protein coupling.

These modified NPY receptors are readily used in a screening assay to detect compounds that bind with high affinity to the NPY receptor subtype, regardless of whether these compounds are agonists or antagonists.

EXAMPLE 8

Cloning and Expression of Modified NPY Receptor cDNA into Bacterial Expression Vectors Recombinant modified receptor is produced in a bacterial expression system such as *E. coli*. The modified receptor expression cassette is transferred into an *E. coli* expression vector; expression vectors include but are not limited to, the pET series (Novagen). The pET vectors place modified receptor expression under control of the tightly regulated bacteriophage T7 promoter. Following transfer of this construct into an *E. coli* host which contains a chromosomal copy of the T7 RNA polymerase gene driven by the inducible lac promoter, expression of modified receptor is induced by addition of an appropriate lac substrate (IPTG) is added to the culture. The levels of expressed modified receptor are determined by the assays described herein.

EXAMPLE 9
Cloning and Expression of Modified NPY Receptor cDNA into a Vector for Expression in Insect Cells Baculovirus vectors derived from the genome of the AcNPV virus are designed to provide high level expression of cDNA in the Sf9 line of insect cells (ATCC CRL# 1711). Recombinant baculovims expressing modified receptor cDNA is produced by the following standard methods (InVitrogen Maxbac Manual): the modified receptor cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., *Nuc. Acid. Res.* 18, 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, modified receptor expression is measured.

Authentic modified receptor is found in association with the infected cells. Active modified receptor is extracted from infected cells by hypotonic or detergent lysis.

Alternatively, the modified receptor is expressed in the Drosophila Schneider 2 cell line by cotransfection of the Schneider 2 cells with a vector containing the modified receptor DNA downstream and under control of an inducible metallothionin promoter, and a vector encoding the G418 resistant neomycin gene. Following growth in the presence of G418, resistant cells are obtained and induced to express modified receptor by the addition of $CuSO_4$. Identification of modulators of the modified receptor is accomplished by assays using either whole cells or membrane preparations.

EXAMPLE 10
Cloning of Modified NPY Receptor cDNA into a yeast expression vector Recombinant modified receptor is produced in the yeast *S. cerevisiae* following the insertion of the modified receptor cDNA cistron into expression vectors designed to direct the intracellular or extracellular expression of heterologous proteins. In the case of intracellular expression, vectors such as EmBLyex4 or the like are ligated to the modified receptor cistron [Rinas, U. et al., *Biotechnology* 8, 543–545 (1990); Horowitz B. et al., *J. Biol. Chem.* 265, 4189–4192 (1989)]. For extracellular expression, the modified receptor cistron is ligated into yeast expression vectors which fuse a secretion signal. The levels of expressed modified receptor are determined by the assays described herein.

EXAMPLE 11
Purification of Recombinant Modified NPY Receptor

Recombinantly produced modified receptor may be purified by a variety of procedures, including but not limited to antibody affinity chromatography.

Modified receptor antibody affinity columns are made by adding the anti-modified receptor antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1 M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents, and the cell culture supernatants or cell extracts containing solubilized modified receptor or modified receptor subunits are slowly passed through the column. The column is then washed with phosphate-buffered saline (PBS) supplemented with detergents until the optical density (A280) falls to background; then the protein is eluted with 0.23 M glycine-HCl (pH 2.6) supplemented with detergents. The purified modified receptor protein is then dialyzed against PBS.

EXAMPLE 12
Cloning and Expression of Modified NPY Receptor in Mammalian Cell System A modified receptor is cloned into a mammalian expression vector. The mammalian expression vector is used to transform a mammalian cell line to produce a recombinant mammalian cell line. The recombinant mammalian cell line is cultivated under conditions that permit expression of the modified receptor. The recombinant mammalian cell line or membranes isolated from the recombinant mammalian cell line are used in assays to identify compounds that bind to the modified receptor.

EXAMPLE 13
Screening Assay

Recombinant cells containing DNA encoding a modified NPY receptor, membranes derived from the recombinant cells, or recombinant modified receptor preparations derived from the cells or membranes may be used to identify compounds that modulate modified NPY receptor activity. Modulation of such activity may occur at the level of DNA, RNA, protein or combinations thereof. One method of identifying compounds that modulate modified NPY receptor, comprises:

(a) mixing a test compound with a solution containing modified NPY receptor to form a mixture;

(b) measuring modified NPY receptor activity in the mixture; and (c) comparing the modified NPY receptor activity of the mixture to a standard.

EXAMPLE 14
Formulation of Pharmaceutical Compositions

Compounds identified by the method of Example 13 are formulated into pharmaceutical compositions according to standard methods. The compounds or pharmaceutical compositions are used either alone or in combination with other compounds or compositions for the treatment of animals (including humans) in need of treatment. Conditions requiring treatment include but are not limited to obesity, regulation of apetite, congestive heart failure, diabetes, anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases.

EXAMPLE 15
Methods of Treatment

Animals (including humans) having a condition, the condition being characterized by factors selected from altered levels of neuropeptide Y, altered activities of neuropeptide Y, altered levels of neuropeptide Y receptor activity, altered neuropeptide Y receptor activity, and combinations thereof, are treated with compounds or derivatives of compounds identified by the screening method or pharmaceutical compositions comprising the compounds or derivatives of compounds identified by the screening method.

Animals (including humans) having a condition selected from obesity, diabetes, anxiety, hypertension, cocaine withdrawal, congestive heart failure, memory enhancement, cardiac vasospasm, cerebral vasospasm, pheochromocytoma and ganglioneuroblastoma, Huntington's Disease, Alzheimer's Disease, Parkinson's disease, and combinations thereof, are treated with a therapeutically effective amount of compounds or derivatives of compounds identified by the screening method or pharmaceutical compositions comprising the compounds or derivatives of compounds identified by the screening method.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. An isolated cDNA encoding a modified neuropeptide Y1 receptor, wherein the modified neuropeptide Y1 receptor is selected from the group consisting of:
    (a) a modified neuropeptide Y1 receptor comprising the amino acid sequence of SEQ ID NO:3, wherein amino acids 234–241 of SEQ ID NO:3 have been deleted; and
    (b) a modified neuropeptide Y1 receptor comprising the amino acid sequence of SEQ ID NO:3, wherein amino acids 247–259 of SEQ ID NO:3 have been deleted.

2. An isolated modified neuropeptide Y1 receptor, wherein the modified neuropeptide Y1 receptor is selected from the group consisting of:
    (a) a modified neuropeptide Y1 receptor comprising the amino acid sequence of SEQ ID NO:3, wherein amino acids 234–241 of SEQ ID NO:3 have been deleted; and
    (b) a modified neuropeptide Y1 receptor comprising the amino acid sequence of SEQ ID NO:3, wherein amino acids 247–259 of SEQ ID NO:3 have been deleted.

* * * * *